(12) United States Patent
Pfeiffer et al.

(10) Patent No.: US 8,334,894 B2
(45) Date of Patent: Dec. 18, 2012

(54) METHOD AND DEVICE FOR OPTICAL SCANNING OF THREE-DIMENSIONAL OBJECTS BY MEANS OF A DENTAL 3D CAMERA USING A TRIANGULATION METHOD

(75) Inventors: Joachim Pfeiffer, Bensheim (DE); Konrad Klein, Heidelberg (DE)

(73) Assignee: Sirona Dental Systems GmbH, Bensheim (DE)

( * ) Notice: Subject to any disclaimer, the term of this patent is extended or adjusted under 35 U.S.C. 154(b) by 610 days.

(21) Appl. No.: 12/563,723

(22) Filed: Sep. 21, 2009

(65) Prior Publication Data

US 2010/0158490 A1    Jun. 24, 2010

(30) Foreign Application Priority Data

Dec. 19, 2008  (DE) .................. 10 2008 054 985

(51) Int. Cl.
*H04N 13/02* (2006.01)
(52) U.S. Cl. ............... 348/46; 382/284; 433/24; 433/29
(58) Field of Classification Search .......... 348/43, 348/46, 47, 48
See application file for complete search history.

(56) References Cited

U.S. PATENT DOCUMENTS

| | | | |
|---|---|---|---|
| 4,575,805 A | 3/1986 | Moermann et al. ............ 364/474 |
| 4,837,732 A | 6/1989 | Brandestini et al. ...... 364/413.28 |
| 5,372,502 A | 12/1994 | Massen et al. ................ 433/215 |
| 6,364,660 B1 | 4/2002 | Durbin et al. .................. 433/29 |
| 6,648,640 B2 | 11/2003 | Rubbert et al. ................. 433/24 |
| 6,885,464 B1 | 4/2005 | Pfeiffer et al. ................ 356/602 |
| 7,349,104 B2 | 3/2008 | Geng ............................ 356/603 |
| 7,365,301 B2 | 4/2008 | Sasaki ........................ 250/208.1 |
| 7,391,522 B2 | 6/2008 | Sasaki ........................... 356/601 |
| 7,494,338 B2 | 2/2009 | Durbin et al. .................. 433/29 |
| 7,522,764 B2 | 4/2009 | Schwotzer |
| 7,978,930 B2 * | 7/2011 | Nakajima et al. ............ 382/284 |
| 2004/0151369 A1 | 8/2004 | Schwotzer |
| 2005/0088435 A1 | 4/2005 | Geng |
| 2006/0192082 A1 | 8/2006 | Sasaki |
| 2006/0246393 A1 | 11/2006 | Eiff et al. |
| 2007/0171220 A1 | 7/2007 | Kriveshko |
| 2009/0021750 A1 | 1/2009 | Korner et al. ................. 356/601 |
| 2010/0157019 A1 | 6/2010 | Schwotzer et al. |
| 2010/0158490 A1 * | 6/2010 | Pfeiffer et al. .................. 396/16 |
| 2010/0284589 A1 | 11/2010 | Thiel et al. |

FOREIGN PATENT DOCUMENTS

| | | |
|---|---|---|
| DE | 198 29 278 C1 | 2/2000 |
| DE | 103 04 111 A1 | 10/2004 |
| DE | 10 2005 020 240 A1 | 11/2006 |
| EP | 0 250 993 A2 | 1/1988 |
| EP | 0 250 993 B1 | 1/1988 |
| JP | 2008-190962 A | 8/2008 |
| WO | 2010012838 A1 | 2/2010 |

* cited by examiner

*Primary Examiner* — Michael Won
(74) *Attorney, Agent, or Firm* — Fitzpatrick, Cella, Harper & Scinto

(57) ABSTRACT

A dental 3D camera for optically scanning a three-dimensional object, and a method for operating a dental 3D camera. The camera operates in accordance with a triangulation procedure to acquire a plurality of images of the object. The method comprises forming at least one comparative signal based on at least two images of the object acquired by the camera while at least one pattern is projected on the object, and determining at least one camera shake index based on the at least one comparative signal.

19 Claims, 2 Drawing Sheets

METHOD AND DEVICE FOR OPTICAL SCANNING OF THREE-DIMENSIONAL OBJECTS BY MEANS OF A DENTAL 3D CAMERA USING A TRIANGULATION METHOD

TECHNICAL FIELD

The invention relates to a method and a device for optical scanning of three-dimensional objects by means of a dental 3D camera using a triangulation method. To this end, several individual images of a pattern projected on the object are recorded.

PRIOR ART

With prior methods, the user has had to fix the moment of initiation by actuating a footswitch and has had to hold the camera still from this moment on for the duration of the exposure. Recording was carried out at the moment of initiation and the result then visualized. When assessing the resulting image, a certain degree of experience was required for recognition of artifacts caused by camera shake and, if necessary, for a decision to erase the recording. The actuation of the footswitch is likely to increase movement at the moment of initiation. The problem of camera shake was thus solved by making a plurality of recordings Until one occurred in which, according to the judgment of the user, no artifacts caused by camera shake could be detected, this being kept for use whilst the other images were deleted.

This is solved in DE 10 2005 020 240 A1 by a delay circuit, which causes scanning to take place only after the elapse of a variable time interval following actuation of the initiating means by the user. In this way, the user has the possibility of resetting the camera into a state of rest following actuation of the initiating means. However, this method also requires the experience of the user for assessment of camera shake in the individual recordings.

The attainment of low-shake recordings is, in fact, one of the main difficulties for the dentist when acquiring competence in the recording method making use of triangulation by means of a handheld camera. Hitherto, the problem has been solved by the experience of the user.

In order to avoid camera shake, the display of a video image as viewfinder image is not purposeful, since the artifacts caused by camera shake cannot be recognized in advance but are only visible after the user has initiated an exposure. This range of problems is described in EP 0,250,993 B1.

The acquisition of tooth geometries with a handheld 3D camera involves the problem of camera shake. Particularly in the case of the intra-oral situation, but also in many situations involving extra-oral scanning of plaster casts, this problem cannot be completely avoided by resting the arms on supports or the like. Camera shake is particularly detrimental in the case of 3D recording using structurized light and the phase shifting method, since in this case a plurality of exposures, usually from 4 to 16 exposures, are required from the same camera position.

In a dental 3D camera disclosed in DE 198 29 278, the monomode range is increased by partially covering a diaphragm mechanically during a scanning sequence, so that scanning cannot be continuously repeated. The camera movements during the individual images as caused by camera shake lead here to wavy artifacts and sometimes completely useless 3D exposures.

SUMMARY OF THE INVENTION

It is an object of the invention to provide a method and device of the aforementioned type which avoids the said drawbacks and assists the user in obtaining almost non-shake images and, in particular, makes it possible to indicate in a suitable manner the occurrence of camera shake in real time and to automatically detect moments at which no camera shake or only slight camera shake of the 3D camera takes place or has taken place.

According to the present invention, the method for optical scanning of three-dimensional objects by means of a dental 3D camera using a triangulation method comprises the following method steps: at least two images of a pattern projected on an object are acquired and at least one comparative signal is determined from these at least two images by means of a camera shake analyzing unit, and a camera shake index is computed from said at least one comparative signal.

This camera shake index provides an objective measure of the camera shake and can therefore be used for assessment of the quality of the optical scan.

A 3D data set can be made from a scanning sequence consisting of at least two images of the pattern projected on the object, and advantageously at least one of the images used for computation of the camera shake index forms part of the scanning sequence.

The use of images from the scanning sequence for computation of the camera shake index avoids the possibility of recording images merely for determining camera shake and then deleting them without using them for making the 3D data set.

Advantageously, the pattern can have a periodically phased brightness distribution and a phase relationship which is known relative to an illuminating ray. The brightness distribution is advantageously sinusoidal. The pattern can consist, for example, of parallel stripes showing a sinusoidal brightness distribution.

The brightness distribution can advantageously at least approximate a sinusoidal distribution, in order to make it possible to use common evaluation algorithms.

The patterns of the at least two images used for computation of the camera shake index can advantageously have a relative phase position which is identical or is phase-shifted by a multiple of a half period of the pattern.

This makes for simple computation of the camera shake index.

Advantageously, the individual images consist of a plurality of pixels showing levels of intensity or grayness, each pixel being associated with a pair of coordinates. The camera shake analyzing unit can form comparative signals from these images by division or subtraction, in which process two images showing a suitable phase position are used and the quotient or difference is formed for the levels of intensity of the images, pixel by pixel, such that the comparative signal again consists of a plurality of pixels.

The comparative signal can be formed by subtraction. To this end, the levels of intensity of a first image can be subtracted from the levels of intensity of a second image, pixel by pixel, so that the comparative signal shows a two-dimensional distribution.

Advantageously, comparative signals can be determined by forming the difference between two images that are mutually out of phase by a half period of the pattern.

Since they are in mirror relationship to each other, subtraction leads in the case of sinusoidal signals to halving of the period with unchanged amplitude, if no camera shake has taken place. When a time-dependent camera shake of the 3D camera occurs, the comparative signal changes.

Instead of a difference, a quotient can be formed, in which case advantageously images showing the same phase position of the pattern are used.

Advantageously, division can be carried out, pixel by pixel, according to formula $(1-q1/q2)$.

In a further step, a camera shake index can be computed from at least two comparative signals, to which end at least three images are implemented.

This camera shake index is a reliable indication of camera shake of the 3D camera within a period of time elapsing between the exposures of the at least two images used for computation of the camera shake index.

Advantageously, merely a representative selection of pixels in the comparative signals can be used for computation of the camera shake index.

Thus the quality of the signal, i.e. of the camera shake index, is improved in, say, the center of the image.

Advantageously, computation of the camera shake index can be effected by forming the variance between the corresponding pixels of two images of identical phase position, in which case the squared deviations computed for computation of the variance are squares of the distances between corresponding pixels in the images being compared.

For this reason, the sum of the squared deviations, and thus also the variance, increases with increased camera shake so that the variance can be regarded as a suitable indicator of the degree of camera shake of the 3D camera.

Advantageously, the user can execute an initiation request by actuating initiating means such that, within a given subsequent time window, images can be continuously recorded both for scanning sequences and for computation of the camera shake index and these are temporarily stored in an image memory while the camera shake index is continuously computed. A moment of initiation at which there was minimum camera shake can be selected and computation of a 3D image from the individual images in the preceding scanning sequence can be initiated.

In this way, the user can approximately fix the moment of exposure, while he tries to keep the 3D camera still following execution of the initiation request.

Advantageously, the specified time window can be up to two seconds. By this means the user will have adequate time to steady the 3D camera following actuation of the initiating means.

An advantageous development of the initiating means consists in that the user can execute an initiation request by actuating initiating means such that, within a given subsequent time window, images both for a scanning sequence and for computation of the camera shake index are continuously recorded while the camera shake index is continuously computed and compared with the threshold value, and computation of at least one 3D data set from the images in the last scanning sequence is initiated when said index falls short of said threshold value and the 3D camera is thus in a relatively steady position.

In this way, the moment of scanning, i.e. the moment of exposure of the scanned data set used for computation of the 3D data set, can be determined by the user by steadying the 3D camera and allowing the camera shake index to fall short of a fixed threshold value. Such steadying typically rarely occurs accidentally. In this way it is possible to achieve considerable simplification of the scanning process, particularly in the case of a plurality of consecutive individual exposures for a 3D data set, since it is no longer necessary to monitor the results of the individual exposures.

Advantageously, the specified time window can here again be up to two seconds, in order to give the user adequate time to steady the 3D camera following actuation of the initiating means.

Advantageously, a variable threshold value for the camera shake index can be established.

Advantageously, the threshold value, starting from an initial value, can be raised within a fixed time window until the measured camera shake index falls short of the threshold value and consequently the computation of a 3D data set is initiated.

This can ensure that the measured camera shake index is under-run at at least one moment within the time window and that at least one computation of a 3D data set will be initiated.

An advantageous development of the initiating means consists in that following actuation of the initiating means by the user, each falling short of the threshold value during the entire time window of the scanning operation causes, without further initiation requests from the user, a 3D data set to be computed from the images in the preceding scanning sequence, which data set is then saved. The plurality of 3D data sets can then be combined to form one overall 3D recording.

By this means, the user needs to initiate the scanning operation only once, and a number of 3D scans will occur whenever the user holds the 3D camera still and the camera shake index thus falls short of the threshold value.

Advantageously, at least five images with different phase positions of the pattern can be recorded, whereat at any one time the phase position is shifted by one quarter of the period of the pattern, that is to say, a first phase-related image with a phase position of 0° is recorded, then a second image with a phase position of 90°, a third image with a phase position of 180°, a fourth image with a phase position of 270° and finally a fifth image with a phase position of 360°. Thus the phase position of the final image corresponds to that of the image first recorded.

Advantageously, the first four images recorded form a scanning sequence, from which a 3D data set can be made by the phase shifting method.

A camera shake index can be advantageously computed by means of the camera shake analyzing unit from these five images recorded with the 3D camera, to which end a first comparative signal between the image of the second phase position and that of the fourth phase position is formed and a second comparative signal between the image of the first phase position and that of the third phase position is formed and a third comparative signal between the image of the third phase position and that of the fifth phase position is formed, in each case by subtraction, and the camera shake index is then computed by averaging a first signal variance between the first comparative signal and the second comparative signal and a second signal variance between the first comparative signal and the third comparative signal over a specific selection of a plurality of pixels, which camera shake index is implemented for the assessment of the degree of camera shake of the 3D camera during optical scanning.

When the 3D camera is in a position of rest, the first comparative signal between the second and fourth phase positions, the second comparative signal between the first and third phase positions, and the third comparative signal between the third and fifth phase positions have a sinusoidal shape with the same amplitude and half period as shown by the image signal of the pattern. Only when there is a time-dependent change in position of the 3D camera relative to the object being scanned is there a noticeable difference between the comparative signals. Consequently there is an increase in the first signal variance between the first comparative signal and the second comparative signal and also in the second signal variance between the first comparative signal and the third comparative signal, so that the average camera shake index rises. In this way the camera shake index is a reliable indicator of the camera shake of the 3D camera within a scanning sequence.

Advantageously, the camera shake analyzing unit can be implemented to compute a camera shake index from two images recorded with the 3D camera and having the same phase position, to which end a comparative signal can be formed by division according to formula (1-q1/q2) between the two images, and the camera shake index can be computed over a representative selection of a plurality of pixels of this comparative signal, which camera shake index is implemented for the assessment of the degree of camera shake of the 3D camera during the optical scan.

When the 3D camera is in a position of rest, the two images have the same phase position. Only when there is a time-dependent change in position of the 3D camera relative to the object being scanned do the two images differ from each other. Consequently, the quotient of the two images according to the aforementioned formula will deviate from zero and the camera shake index will rise. This means that the thus determined camera shake index is likewise a reliable indicator of the camera shake of the 3D camera within a scanning sequence.

For the purpose of visualizing the camera shake, a high-contrast image can be computed from at least two comparative signals that have been determined from at least three images of the pattern projected on the object and can be outputted. The oscillating camera movements typical of a handheld camera appear as a time-varying jitter.

This makes it possible for the user to observe the intensity of the camera shake in real time and to determine the moment of initiation correspondingly. The indicating device can be, say, a monitor.

Advantageously, the formula for computation of the high-contrast image can be $K=\sqrt{(Im^2+Re^2)}$ wherein Im denotes the first comparative signal and Re the second comparative signal.

Advantageously, the computed comparative signals can be temporarily stored in a data storage device and used for computation of another high-contrast image, in which the comparative signals from different scanning sequences are compared.

In order to obtain time-dependent visualization of the camera shake, two comparative signals determined from two images can be taken for continuous computation of a high-contrast image, which can be outputted, and, advantageously, use is always made of the last comparative signal to have been used and a subsequently determined comparative signal. The continuously outputted high-contrast images appear as a time-varying jitter.

The user can thus construe the degree of camera shake of the 3D camera in real time from the intensity of the jitter.

Advantageously, the high-contrast image is continuously computed and displayed over time and can be used by the user for choosing the moment of initiation for computation of the 3D data set from the individual images of a scanning sequence.

The high-contrast image thus allows for objective assessment of the degree of camera shake of the camera without previous experience, in order to recognize camera shake from the occurrence of artifacts in a viewfinder image known from the prior art.

Advantageously, at least four images can be used for computation of the high-contrast image (12), wherein the phase position (40, 41, 42, 43, 44) of the pattern (3) in each image is shifted by +90° relative to the preceding image so that the first phase position (40) of the first image is 0°, the second phase position (41) of the second image is 90°, the third phase position (42) of the third image is 180° and the fourth phase position (43) of the fourth image is 270°.

From the four images it is then possible to acquire two comparative signals by subtraction, a first comparative signal (45) being formed from the images of a second phase position (41) and a fourth phase position (43) and a second comparative signal (46) being formed between the images of a first phase position (40) and a third phase position (42). Subsequently, for the purpose of visualization of the camera shake, a high-contrast image (12) can be computed from the first comparative signal (45) and the second comparative signal (46) preceding the first comparative signal (45), which high-contrast image (12) can be outputted on an indicating device (11).

Advantageously, optical scanning can be carried out using double triangulation, computation of an individual 3D data set being carried out by implementation of the first scanning sequence using a first triangulation angle and then of a second scanning sequence using a second triangulation angle.

The second scanning sequence can serve, for example, to enlarge the depth scanning range in that the monomode range is enlarged. This is known per se. In the context of the present invention, however, the second scanning sequence will only be initiated when the camera shake of the first scanning sequence is sufficiently small.

In the method of double triangulation, projection of the pattern onto the object is carried out at two different triangulation angles and recorded. In this way the uniquely assignable depth scanning range is increased distinctly. For this purpose, the first triangulation angle can be between 1° and 13° and the second triangulation angle between 1.5° and 15°. The unique depth scanning range can be between 20 mm and 25 mm.

Advantageously, according to the method of double triangulation, a second scanning sequence using a second triangulation angle can be recorded once the threshold was under-run, after which a 3D data set can be computed from the images in a first scanning sequence, prior to the point of falling short of the threshold value, and from images in the second scanning sequence.

A 3D data set can, according to the invention, be alternatively produced by using the light-section method, in which case a plurality of individual images of a plurality of patterns (3) projected on the object (2) are recorded to form a scanning sequence. From the positions of sub-patterns detected in the images of a scanning sequence geometric acquisition takes place and the 3D data set is computed.

According to the invention, at least one further image of the object showing one of the patterns is recorded, and this further image is used together with the image in the scanning sequence showing the corresponding pattern for determination of the camera shake index (50).

As another object of the invention, the invention relates to a device for optical scanning of three-dimensional objects by means of a dental 3D camera using a triangulation method, a dental 3D camera, and a camera shake analyzing unit. The device is capable of recording at least two individual images of a pattern projected on the object. The device has a camera shake analyzing unit, and by means of the camera shake analyzing unit for determination of the camera shake of a handheld 3D camera at least one comparative signal can be acquired by division or subtraction of the at least two individual images, and a camera shake index can be computed from the at least one comparative signal.

This device of the invention is primarily suitable for the purpose of carrying out the process of the invention as defined in claim 1.

By means of said device a scanning sequence consisting of at least two images recorded with the 3D camera is recorded and saved to a memory. Furthermore a 3D data set can be made from the images in the scanning sequence, whilst at least one of the images used for computation of the camera shake index can be part of the scanning sequence.

This has the advantage that a minimum of extra processing is necessary for ascertaining the degree of camera shake.

The device can have a pattern which can advantageously show a brightness distribution having periodic phases and a known phase relationship and a known phase position relative to an illuminating ray.

In particular, the brightness distribution can consist of parallel stripes showing a sinusoidal intensity gradient.

Advantageously, the device can have initiating means, and the user can, by actuating the initiating means, initiate scanning and the computation of an individual 3D data set within a specified time window or alternatively scanning and the computation of a plurality of 3D data sets within the specified time window. The duration of the time window is stored in a memory in the camera shake analyzing unit.

The initiating means can, for example, be a foot pedal or any desired actuating element.

Advantageously, the device can have an image processing unit, in which case the camera shake analyzing unit initiates computation of the 3D data set from the images in the selected scanning sequence in an image processing unit.

The image processing unit can be a data processing unit, such as a computer running special software for signal processing, or an electronic circuit.

Advantageously, the camera shake analyzing unit can comprise a memory in which a variable threshold value can be stored.

Advantageously, the device can comprise regulating means for changing the triangulation angle in order to make it possible to carry out optical scanning using the method of double triangulation involving a first scanning sequence at a first triangulation angle and a second scanning sequence at a second triangulation angle.

Such regulating means for changing the triangulation angle can be a mechanical flag for partial cut-off of the illuminating ray, some other electronically controlled Optical shield, or alternatively another light source, such that the regulating means causes the illuminating ray to come from a different direction and in this way alters the triangulation angle.

The computed comparative signals can be stored in a data storage device present in the camera shake analyzing unit.

Advantageously, the device can have indicating means, which can be in the form of a monitor, and a high-contrast image of at least two comparative signals can be computed for visualization of the camera shake, which comparative signals can be acquired, by subtraction or division, from at least three images of the pattern projected on the object. The high-contrast image can be indicated by the indicating means as a simultaneously displayed number of measured values depicting pixel intensities, the camera shake appearing in the form of a time-varying jitter. The camera shake analyzing unit can be designed such that it is suitable for computation of the high-contrast image.

The camera shake analyzing unit can be installed in the 3D camera or remote therefrom in data processing equipment connected to the 3D camera by a cable or a radio connection. The camera shake analyzing unit can be a computer running software specially adapted for signal processing, or alternatively an electronic circuit adapted to process incoming signals in a prescribed manner and to emit an output signal. This camera shake analyzing unit computes, for example, the camera shake index in said manner by comparing the incoming signals from the individual images with each other by differential analysis.

An advantage of the method of the invention is that the analysis of the camera shake does not take place after scanning, i.e. after a 3D data set has been compiled, by looking for typical artifacts caused by camera shake, but is carried out prior to computation of the 3D data set. In this way, a 3D data set is only computed when only slight camera shake of the 3D camera is detected.

Another advantage is that the assessment of the degree of camera shake is not carried out subjectively according to the opinion of a user but takes place on the basis of objectively measurable criteria, so that the quality of the 3D data set is assured and errors due to human inobservance or inexperience are excluded.

BRIEF DESCRIPTION OF THE DRAWINGS

An exemplary embodiment of the invention is shown in the drawings, in which.

EXEMPLARY EMBODIMENTS

Figure 1:
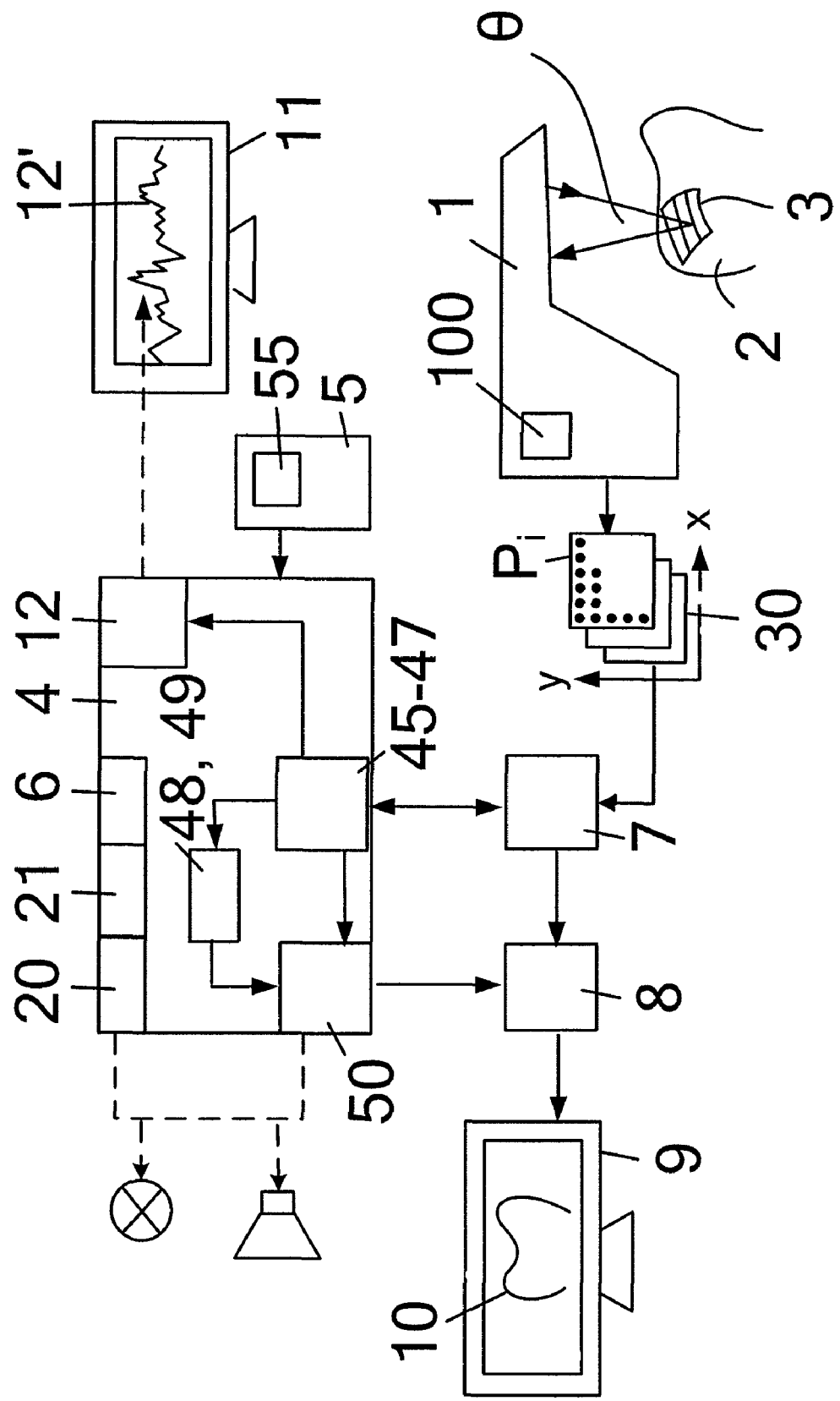
FIG. 1 is a diagram for clarification of the method of the invention showing an initiating means and an automatic initiation and FIG. 2 is a graphical representation to clarify the computation of the camera shake index.

FIG. 1 is a diagram for clarification of the method of the invention and the device of the invention as exemplified by the phase shifting method. A dental 3D camera 1 is used in order to scan a three-dimensional object 2, namely a tooth, using a triangulation method. A viewfinder image, not shown but known from the prior art, makes it possible to position the 3D camera 1 over the object 2. The 3D camera 1 can then record five individual images 30 of the pattern 3 projected on the object 2, which pattern 3 can consist of parallel stripes having a sinusoidal brightness distribution, and the images 30 can each contain a plurality of pixels $P_i$ having the coordinates ($x_i$, $y_i$). For each image 30 the pattern 3 can be shifted by a quarter of a period, i.e. a phase of 90°, the first four of the five images 30 forming a scanning sequence, from which a 3D data set 10 of the object 2 can be computed.

The recorded images 30 can be transmitted by the 3D camera 1 to an image memory 7 and can be evaluated by a camera shake analyzing unit 4 in which the data pertaining to the images 30 are implemented for computation of a camera shake index 50. To this end, comparative signals 45, 46, 47 can be determined by subtraction or division between individual images 30 at corresponding phase positions 40, 41, 42, 43, 44 and can be stored in a data storage device 21. The camera shake index 50 can be determined by averaging or subtracting these comparative signals 45, 46, 47 and by carrying out further averaging over a relevant selection of a plurality of pixels $P_i$. The way in which the computation is carried out is explained in greater detail with reference to FIG. 2.

When the user actuates the initiating means 5, which in the present embodiment can be a footswitch, an initiation request is sent to the camera shake analyzing unit 4. Within a specified time window of, say, 2 seconds, the duration of which is stored in a data storage device 6, images 30 are recorded and placed in an image memory 7, and the camera shake index 50 is computed.

It is then possible to determine a moment of initiation with the lowest camera shake index 50 within the time window and the four images 30 of the scanning sequence preceding said moment of initiation can be fetched from the image memory 7 and passed on to an image processing unit 8. A 3D data set 10 can be computed in the image processing unit 8 from the four individual images 30 by the phase shifting method known per se.

The 3D data set 10 contains the three-dimensional data pertaining to the recorded object 2 and is displayed on an indicating device 9 as a three-dimensional model of the scanned object 2, namely a tooth.

In another embodiment, the computed camera shake index 50 can, within the time window following actuation of the initiating means 5, be compared with a variable threshold value stored in the memory 20, and in the case of a falling short of the threshold value, the computation of the 3D data set 10 of images 30 from the preceding scanning sequence is initiated.

The camera shake analyzing unit 4 can in addition compute a high-contrast image 12 from the first comparative signal 45 and either from the second, preceding comparative signal 46 or from the third, succeeding comparative signal 47 of the individual images 30 and can be shown by means of an indicating device 11 as a time-varying jitter 12'. The high-contrast image 12 reproduces the camera shake of the 3D camera in real time. The user can thus directly watch the fluctuations of the camera shake with time. The user can utilize this high-contrast image 12, for example, in order to assess the degree of camera shake and, for example, to initiate computation of the 3D data set 10 from images 30 in the preceding scanning sequence by again actuating the initiating means 5 at a moment of low camera shake as indicated by the high-contrast image 12.

The data storage device is advantageously large enough to store the data of all comparative signals computed during the entire optical scanning operation.

In addition, the camera shake index can be outputted, for example, in the form of a lamp signal or an acoustic signal. For example, the camera shake index can be continuously compared with the threshold value and, depending on whether it falls short of or exceeds the threshold value, the lamp will emit light or not.

Figure 2:
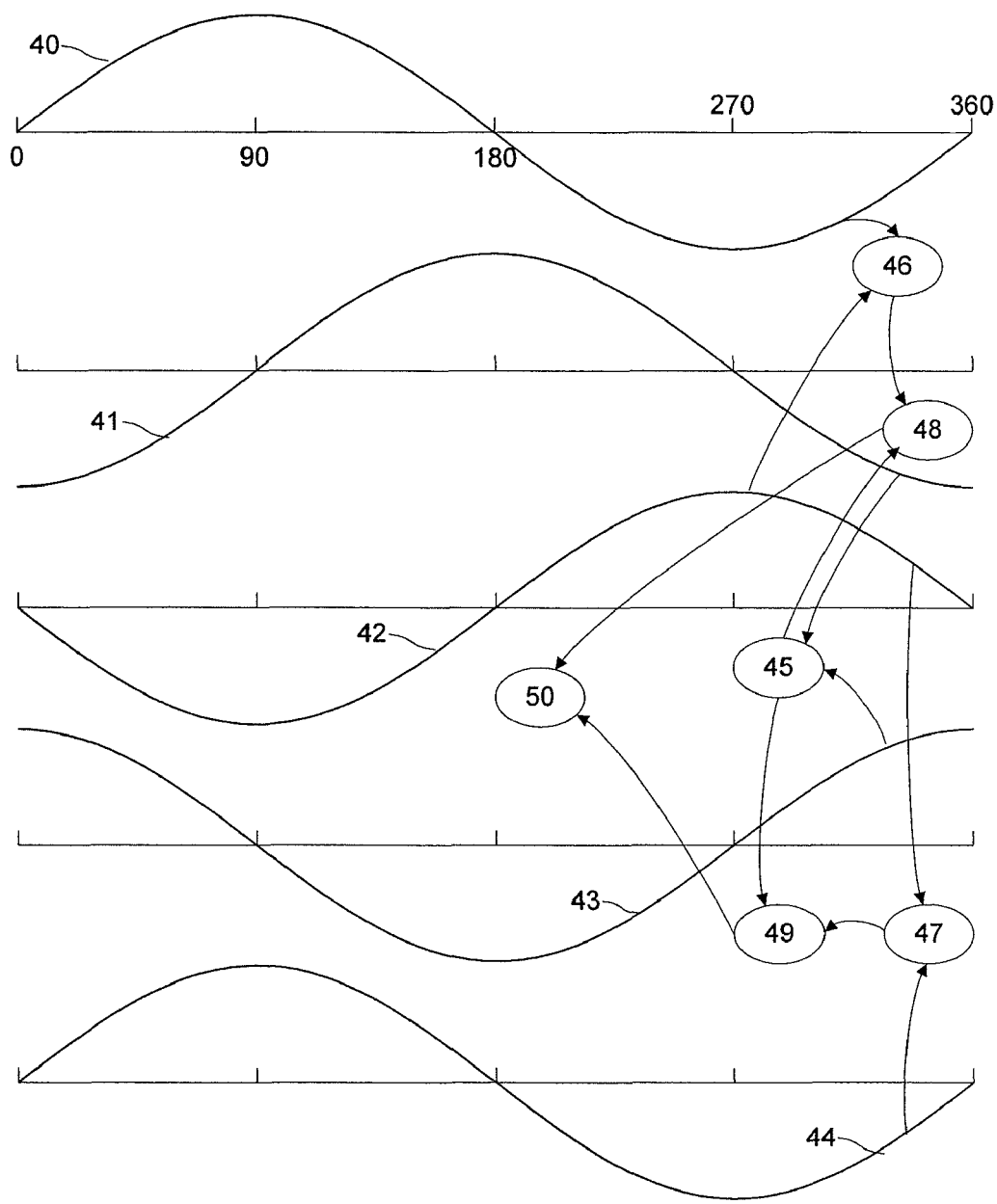

FIG. 2 is a diagrammatic representation for clarification of the computation of the camera shake index 50 and the high-contrast image 12 as exemplified by the phase shifting method. The first phase position 40 of the first image 30 is 0°, the second phase position 41 of the second image 30 is 90°, the third phase position 42 of the third image 30 is 180°, the fourth phase position 43 of the fourth image 30 is 270°, and the fifth phase position of, the fifth image 30 is 360°. A first comparative. signal 45 is formed by the addition of the phasing 41 of the second image 30 to the phasing 43 of the fourth image 30. A second comparative signal 46 is formed by the addition of the phasing 40 of the first image 30 to the phasing 42 of the third image 30. A third comparative signal 47 is formed by the addition of the phasing 42 of the third image 30 to the phasing 44 of the fifth image 30. A first signal variance 48 is formed from the first comparative signal 45 and the second comparative signal 46, a second signal variance is formed from the first comparative signal 45 and the third comparative signal 47, and the camera shake index 50 is computed by averaging over a relevant range of pixels $P_i$.

LIST OF REFERENCE NUMERALS OR CHARACTERS 1 dental 3D camera
2 object
3 pattern
4 camera shake analyzing unit
5 initiating means
6 data storage device for the duration of the scanning time window
7 image memory
8 image processing unit
9 indicating device for indication of the 3D data set
10 3D data set
11 indicating device for indication of the high-contrast image
12 high-contrast image
20 memory for the threshold value
21 data storage device for the comparative signals
30 images having pixels $P_i$ and having levels of intensity or grayness $q_i$
40 first phase position
41 second phase position
42 third phase position
43 fourth phase position
44 fifth phase position
45 first comparative signal
46 second comparative signal
47 third comparative signal
48 first signal variance
49 second signal variance
50 camera shake index
55 switch
100 regulating means This application claims the benefit of priority based on German Patent Application No. 10 2008 054 985.1, filed Dec. 19, 2008, which is hereby incorporated by reference in its entirety, as if set forth fully herein.

The invention claimed is:

1. A method for optically scanning a three-dimensional object with a dental 3D camera that operates in accordance with a triangulation procedure to acquire a plurality of images of the object, the method comprising:
    forming at least one comparative signal based on at least two images of the object acquired by the camera while at least one pattern is projected on the object; and
    determining at least one camera shake index based on the at least one comparative signal,
    wherein the images include a plurality of pixels having coordinates showing levels of intensity or grayness, the at least one comparative signal comprises a plurality of pixels, and the forming of the at least one comparative signal includes dividing or subtracting two images of the at least one pattern of respective phase positions to obtain a quotient or difference, respectively, formed for levels of intensity of those images on a pixel-by-pixel basis.

2. The method as defined in claim 1, further comprising:
    obtaining at least one scanning sequence, each formed by at least one respective group of the images of the object acquired while the at least one pattern is projected on the object, wherein the forming of the at least one comparative signal is performed for each scanning sequence, based on the group of images of that sequence, and
    the determining also includes determining whether the at least one camera shake index, determined with respect to each respective scanning sequence, satisfies predetermined acceptability criterion; and providing a 3D data set based on at least some of the scanning sequences for which the at least one camera shake index satisfies the predetermined acceptability criterion.

3. The method as defined in claim 1, wherein the at least one pattern has a brightness distribution with periodic phasing and a predetermined phase position relative to an illuminating ray, and the brightness distribution includes parallel stripes having a sinusoidal intensity gradient.

4. The method as defined in claim 3, wherein the phase position of the at least one pattern in one of the at least two images is substantially identical to the phase position of the at least one pattern in another of the at least two images, or is shifted therefrom by a multiple of about half a period of the at least one pattern.

5. The method as defined in claim 1, wherein the determining of the at least one camera shake index includes forming a variance of corresponding pixels of the at least two images.

6. The method as defined in claim 1, wherein the forming includes forming at least two comparative signals based on at least three images of the object acquired by the camera while the at least one pattern is projected on the object, and the determining is performed based on the at least two comparative signals.

7. The method as defined in claim 1, further comprising:
initiating an initiation request by actuating an initiator;
within a predetermined time period, obtaining continuous scanning sequences formed by images of the object, acquired while the at least one pattern is projected on the object, wherein the forming of the at least one comparative signal is performed based on at least some of those images; and
in response to a least value of the at least one camera shake index being identified, providing a 3D data set based on images in at least one of the scanning sequences obtained prior to identification of the least value.

8. The method as defined in claim 1, further comprising:
initiating an initiation request by actuating an initiator;
after the initiation request, obtaining continuous scanning sequences formed by images of the object, acquired while the at least one pattern is projected on the object, wherein the forming of the at least one comparative signal is performed based on at some of those images; and
in response to the at least one camera shake index falling below a threshold, providing a 3D data set based on images in at least one of the scanning sequences.

9. The method as defined in claim 8, wherein the threshold is variable.

10. The method as defined in claim 8, wherein the threshold increases at a constant rate until the at least one camera shake index falls below the threshold.

11. The method as defined in claim 1, further comprising:
initiating an initiation request by actuating an initiator; and
after the initiation request,
obtaining continuous scanning sequences formed by images of the object, acquired while the at least one pattern is projected on the object, wherein the forming of the at least one comparative signal is performed based on at least some of those images,
in response to each separate instance of the at least one camera shake index falling below a threshold, and without requiring further initiation of an initiating request, storing a respective 3D data set formed based on images in at least one of the scanning sequences obtained prior to the respective separate instance of the at least one camera shake index falling below the threshold, and
combining at least some stored 3D data sets to form an overall 3D recording.

12. The method as defined in claim 1, wherein the triangulation procedure is a double triangulation procedure, and wherein the method further comprises, for calculation of a 3D data set, forming a first scanning sequence at a first triangulation angle ($\theta 1$), and subsequently forming a second scanning sequence at a second triangulation angle ($\theta 2$).

13. The method as defined in claim 12, wherein the forming of the second scanning sequence is performed in response to the at least one camera shake index falling below a threshold value, and calculation of the 3D data set is performed based on images of the first scanning sequence acquired prior to the at least one camera shake index falling below the threshold value and based on images of the second scanning sequence.

14. The method as defined in any one of claim 1, wherein the at least one pattern includes plural patterns, and wherein the method further comprises:
obtaining at least one scanning sequence formed by at least some of the images of the object, acquired while respective ones of the patterns are projected on the object; and
performing a geometric acquisition from positions of sub-patterns detected in the images.

15. A portable dental 3D camera device having a triangulation angle ($\theta$), for optically scanning a three-dimensional object to acquire a plurality of images of the object, the device comprising a camera shake analyzing unit, arranged to form at least one comparative signal by determining a quotient or difference of at least two images of the object acquired while a pattern is projected on the object, and to determine at least one camera shake index by averaging the at least one comparative signal, wherein the images include a plurality of pixels having coordinates showing levels of intensity or grayness, the at least one comparative signal comprises a plurality of pixels, and the camera shake analyzing unit determines the quotient or difference by dividing or subtracting the at least two images, which include the pattern of respective phase positions, to obtain a quotient or difference, respectively, formed for levels of intensity of those images on a pixel-by-pixel basis.

16. The device as defined in claim 15, further comprising:
a memory arranged to store a scanning sequence formed by at least two images of the object, acquired while the at least one pattern is projected on the object, the scanning sequence including at least one of the images used to form the at least one comparative signal; and
a processing unit arranged to provide at least one 3D data set based on at least some images of the scanning sequence.

17. The device as defined in claim 16, further comprising an initiator operable to initiate an initiation signal, wherein in response thereto, and within a predetermined time period, the memory stores the scanning sequence and the processing unit provides the at least one 3D data set.

18. The device as defined in claim 17, wherein the camera shake analyzing unit also is arranged to detect a least value of the at least one camera shake index, determined within the predetermined time period, and the processing unit is responsive to such a detection by providing the at least one 3D data set.

19. A dental 3D camera device having a triangulation angle ($\theta$), for optically scanning a three-dimensional object to acquire a plurality of images of the object, the device comprising:
a camera shake analyzing unit, arranged to (a) form at least two comparative signals by dividing or subtracting at least two images of the object, acquired in a scanning sequence while a pattern is projected on the object, (b) generate a high-contrast image signal based on at least some of the comparative signals, and (c) determine a camera shake index based on at least some of the comparative signals;

a processing unit arranged to provide at least one 3D data set based on at least some images of the scanning sequence; and a user-perceptible output device, responsive to the high-contrast image signal to provide an output indicating time-varying jitter, wherein the images include a plurality of pixels having coordinates showing levels of intensity or grayness, the at least two comparative signals comprise a plurality of pixels, and the dividing or subtracting of the at least two images, which include the pattern of respective phase positions, obtains a quotient or difference, respectively, formed for levels of intensity of those images on a pixel-by-pixel basis.

* * * * *